United States Patent
Markworth et al.

(10) Patent No.: US 7,780,704 B2
(45) Date of Patent: Aug. 24, 2010

(54) SPINAL CROSS-CONNECTOR

(75) Inventors: Aaron D. Markworth, Saddle Brook, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 666 days.

(21) Appl. No.: 11/373,386

(22) Filed: Mar. 10, 2006

(65) Prior Publication Data

US 2007/0213721 A1 Sep. 13, 2007

(51) Int. Cl.
*A61B 17/70* (2006.01)

(52) U.S. Cl. ...................... 606/253; 606/279

(58) Field of Classification Search ................ 606/250, 606/251, 252, 253, 264, 267, 269, 270, 276, 606/246, 278–279; 403/64, 169, 170, 174, 403/178
See application file for complete search history.

(56) References Cited

U.S. PATENT DOCUMENTS

| | | | | | |
|---|---|---|---|---|---|
| 2,683,329 | A | * | 7/1954 | Kobler | ...................... 403/174 |
| 3,054,321 | A | | 9/1962 | Macchia | |
| 5,100,420 | A | | 3/1992 | Green et al. | |
| 5,312,405 | A | | 5/1994 | Korotko et al. | |
| 5,330,473 | A | * | 7/1994 | Howland | .................... 606/250 |
| 5,334,203 | A | | 8/1994 | Wagner | |
| 5,498,263 | A | | 3/1996 | DiNello et al. | |
| 5,522,816 | A | * | 6/1996 | Dinello et al. | .............. 606/252 |
| 5,688,272 | A | * | 11/1997 | Montague et al. | .......... 606/252 |
| 5,727,899 | A | * | 3/1998 | Dobrovolny | ................ 403/389 |
| 5,735,851 | A | | 4/1998 | Errico et al. | |
| 5,743,911 | A | * | 4/1998 | Cotrel | ........................ 606/250 |
| 5,989,250 | A | | 11/1999 | Wagner et al. | |
| 6,030,389 | A | | 2/2000 | Wagner et al. | |
| 6,187,005 | B1 | * | 2/2001 | Brace et al. | ................. 606/264 |
| 6,217,578 | B1 | | 4/2001 | Crozet et al. | |
| 6,299,614 | B1 | | 10/2001 | Kretschmer et al. | |
| 6,302,882 | B1 | | 10/2001 | Lin et al. | |
| 6,432,108 | B1 | | 8/2002 | Burgess et al. | |

(Continued)

FOREIGN PATENT DOCUMENTS

WO    WO 0150968 A1    7/2001

OTHER PUBLICATIONS

"connected." Merriam-Webster Online Dictionary. 2009.Merriam-Webster Online. Oct. 15, 2009<http://www.merriam-webster.com/dictionary/connected>.*

(Continued)

*Primary Examiner*—Eduardo C Robert
*Assistant Examiner*—Steven J Cotroneo
(74) *Attorney, Agent, or Firm*—Rahman LLC

(57) ABSTRACT

An assembly and a method of locking a longitudinal member to a cross-connector assembly construct, wherein the assembly comprises a longitudinal member; a flexible clip contacting the longitudinal member; a housing component contacting the flexible clip; a locking mechanism contacting the housing component; and a connecting member contacting the housing component. The flexible clip comprises a flexible bias member adapted to retain the longitudinal member. The flexible clip comprises a socket portion; and a clip portion attached to the socket portion, the clip portion being adapted to retain the longitudinal member, wherein the flexible bias member extends from the clip portion to a bottom region of the socket portion.

21 Claims, 16 Drawing Sheets

U.S. PATENT DOCUMENTS

| | | |
|---|---|---|
| 6,524,310 B1 | 2/2003 | Lombardo et al. |
| 6,736,817 B2 | 5/2004 | Troxell et al. |
| 6,761,721 B2 | 7/2004 | Burgess et al. |
| 6,783,526 B1 * | 8/2004 | Lin et al. .................... 606/250 |
| 6,793,657 B2 | 9/2004 | Lee et al. |
| 6,875,211 B2 | 4/2005 | Nichols et al. |
| 6,890,334 B2 | 5/2005 | Brace et al. |
| 7,524,326 B2 | 4/2009 | Dierks |
| 2003/0163133 A1 | 8/2003 | Altarac et al. |
| 2004/0049188 A1 | 3/2004 | Slivka et al. |
| 2005/0070918 A1 | 3/2005 | Zwirnmann et al. |
| 2005/0113831 A1 | 5/2005 | Franck et al. |
| 2005/0192572 A1 | 9/2005 | Abdelgany et al. |
| 2005/0192573 A1 | 9/2005 | Abdelgany et al. |
| 2005/0228377 A1 | 10/2005 | Chao et al. |
| 2005/0234450 A1 * | 10/2005 | Barker .......................... 606/61 |
| 2007/0049932 A1 * | 3/2007 | Richelsoph et al. .......... 606/61 |

OTHER PUBLICATIONS

"concave." Merriam-Webster Online Dictionary. 2009.Merriam-Webster Online. Oct. 15, 2009<http://www.merriam-webster.com/dictionary/concave>.*

* cited by examiner

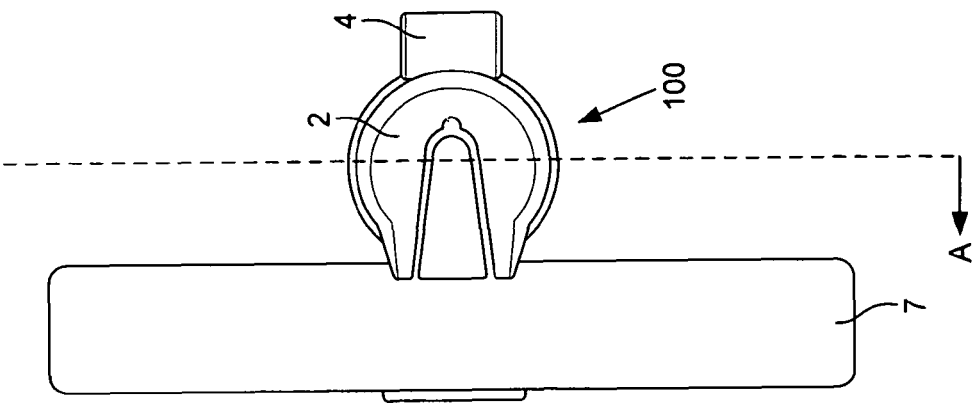
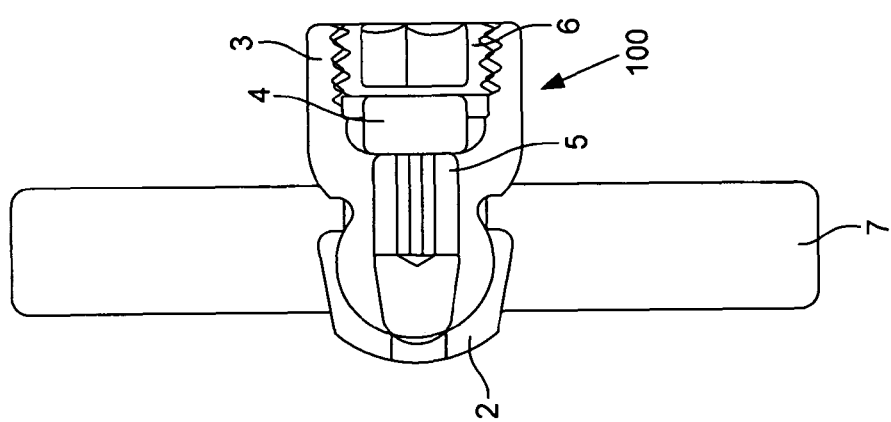
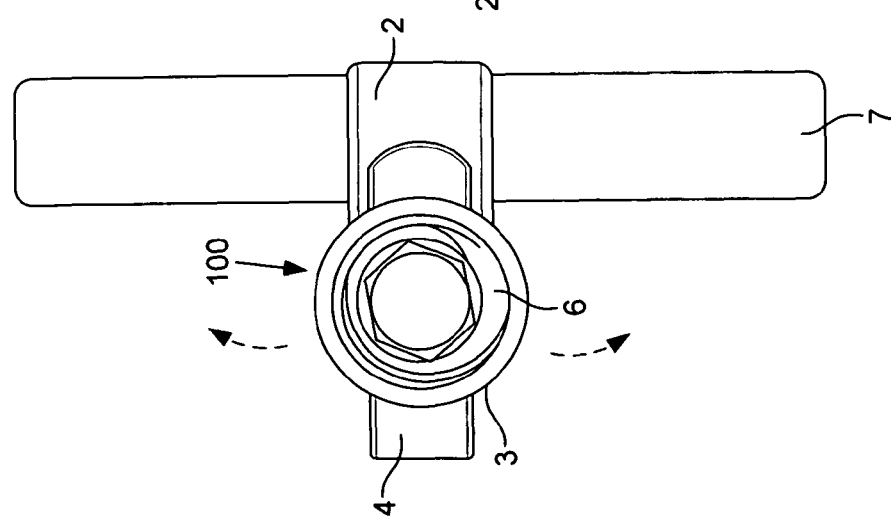

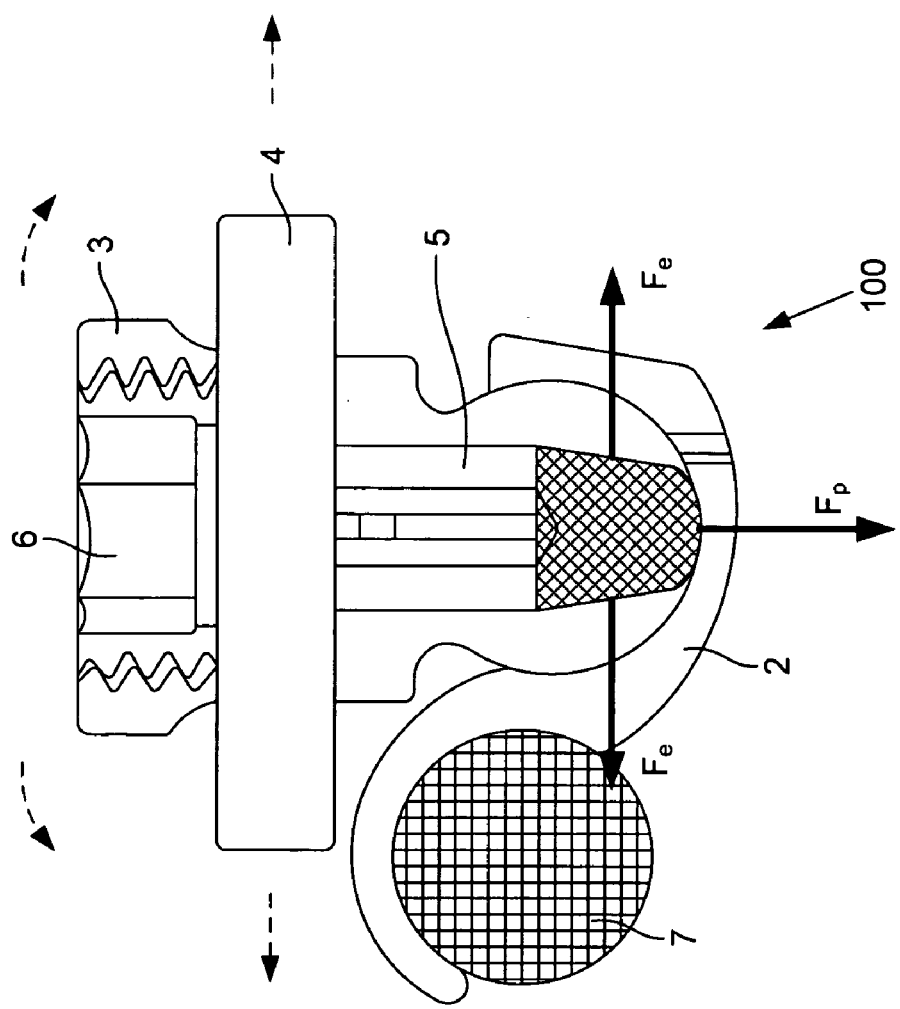

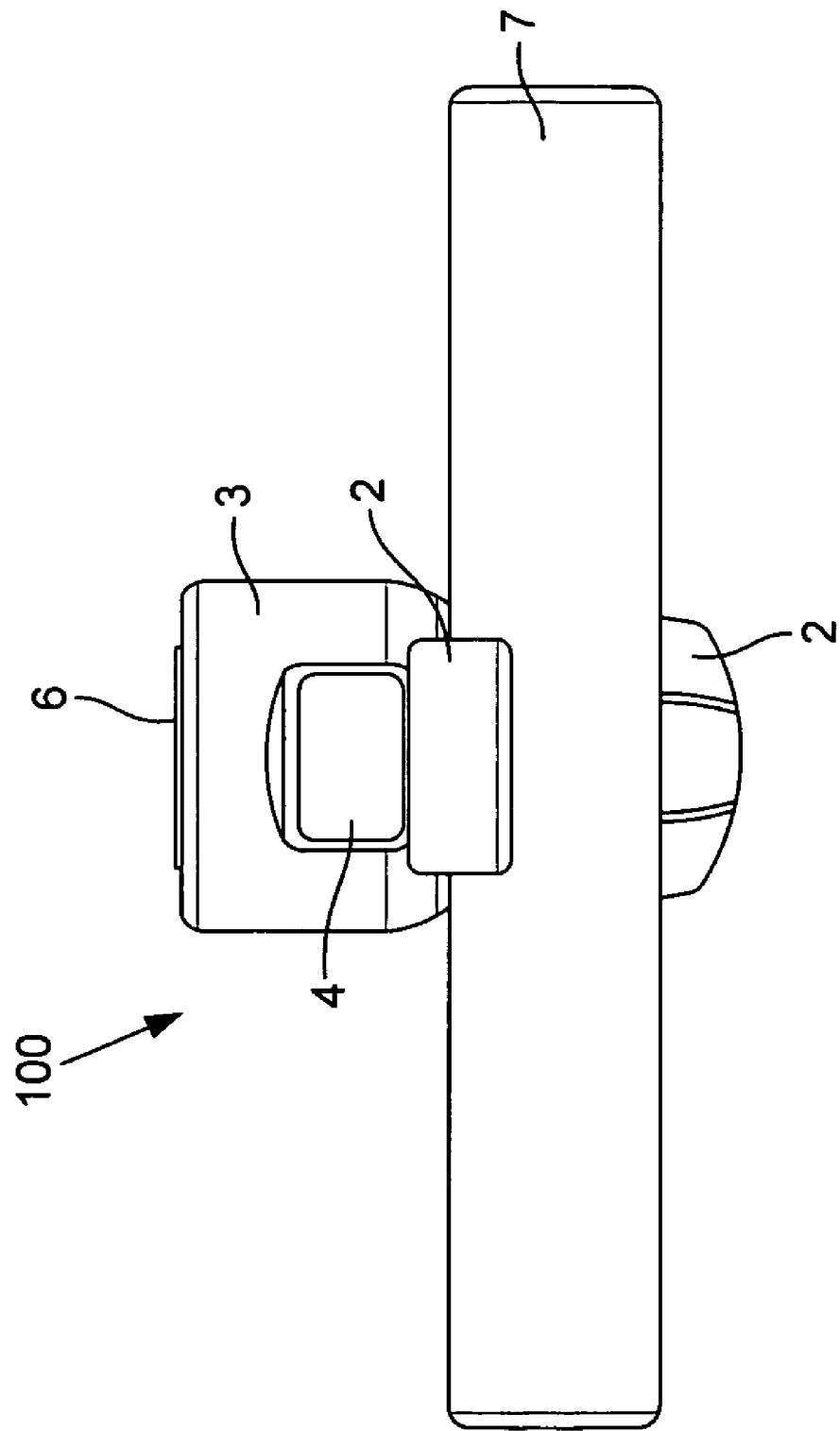

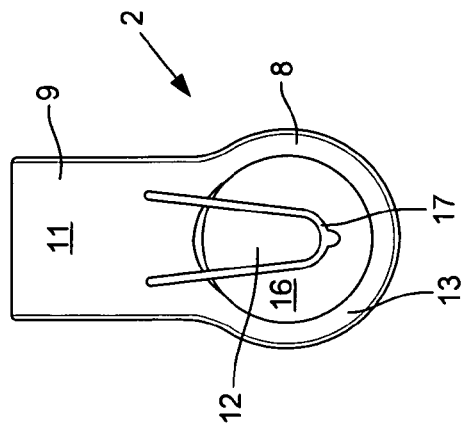
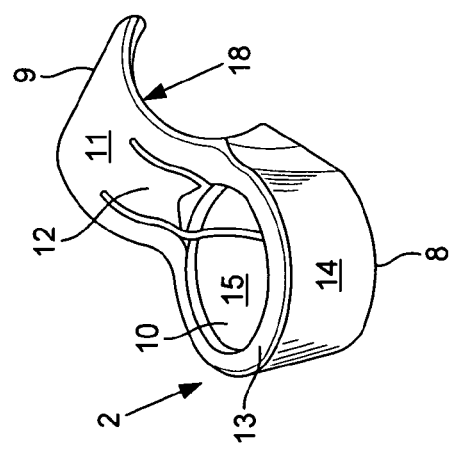
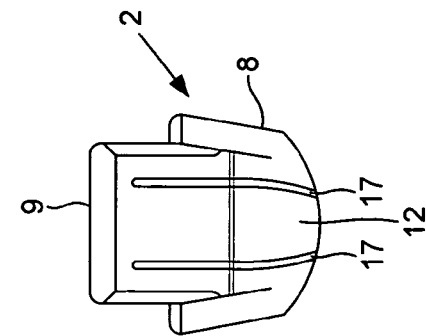
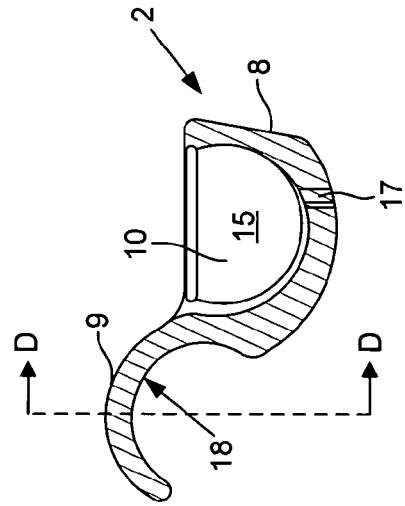
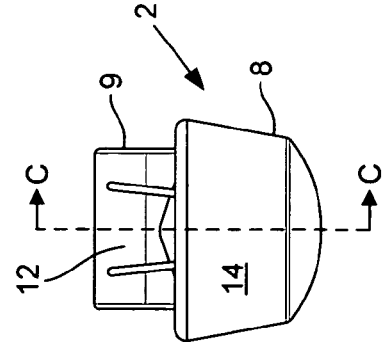

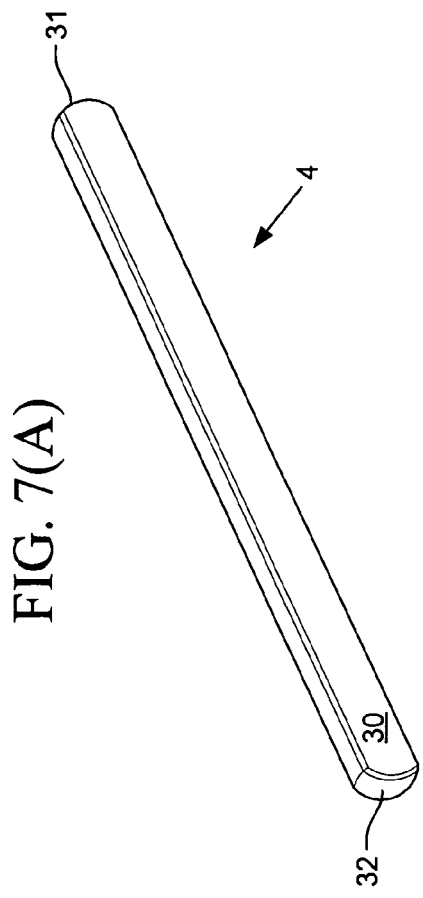
FIG. 7(A)
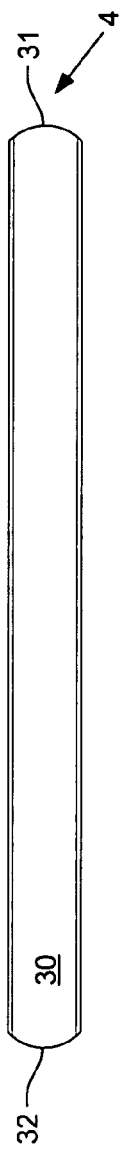
FIG. 7(B)
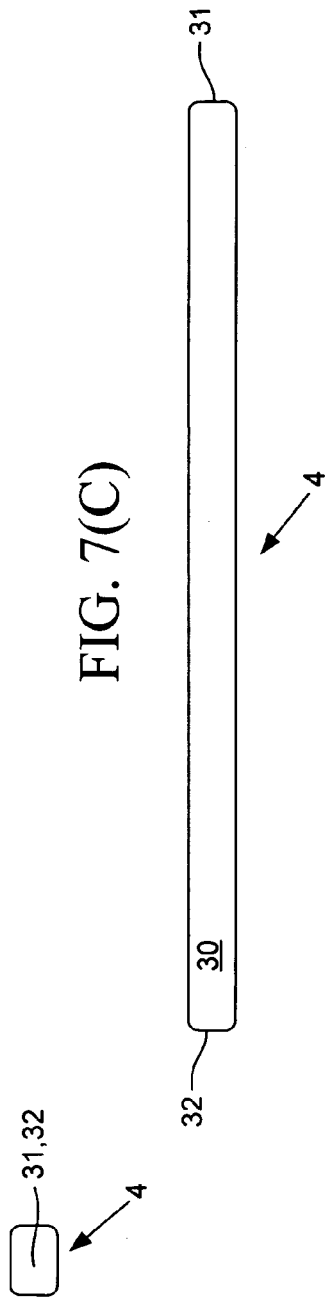
FIG. 7(C)
FIG. 7(D)

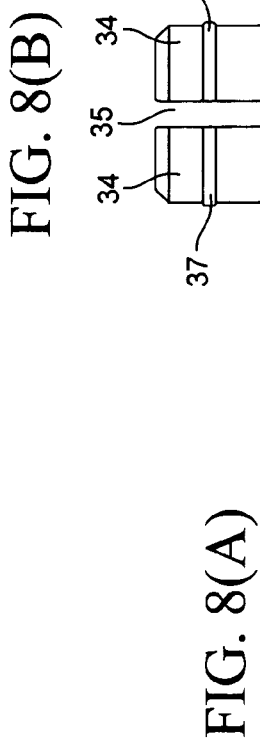
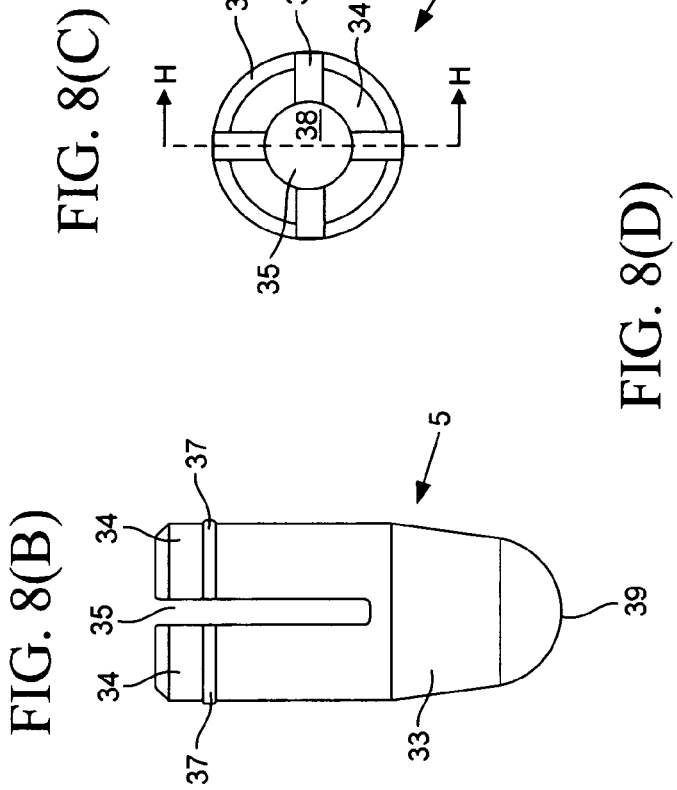
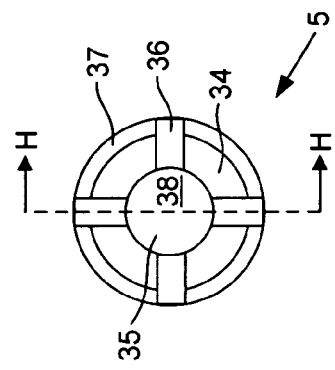
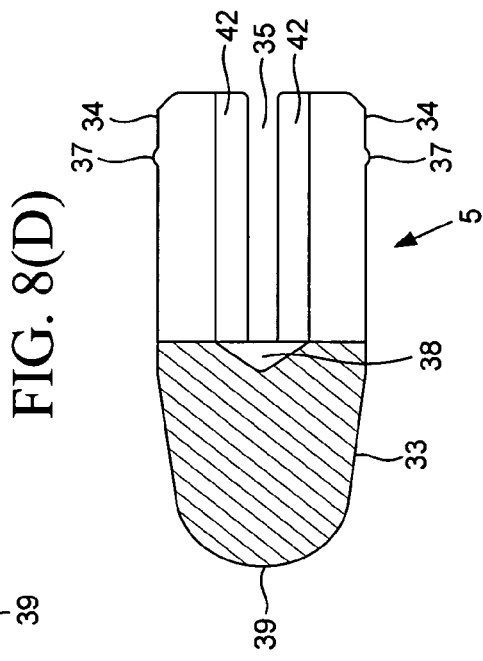
FIG. 8(A)
FIG. 8(B)
FIG. 8(C)
FIG. 8(D)

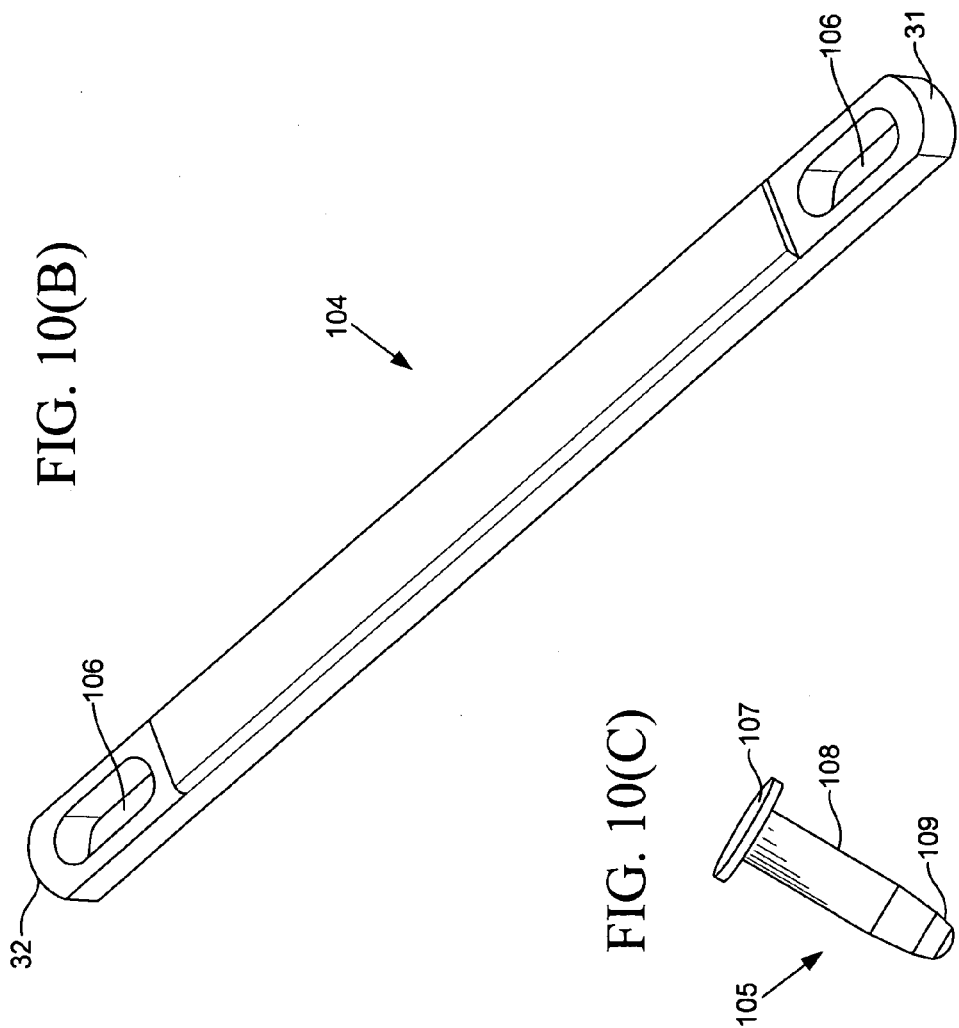

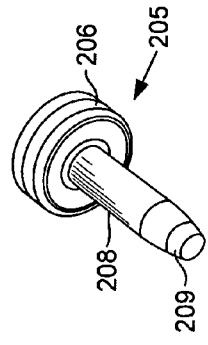
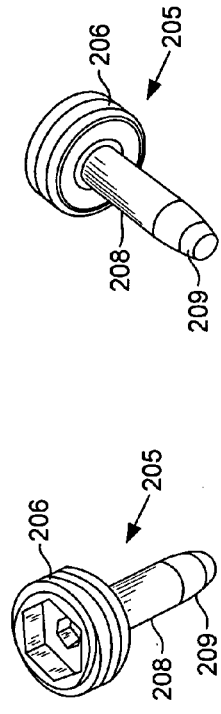
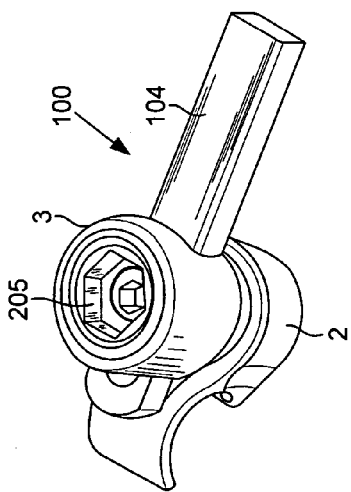
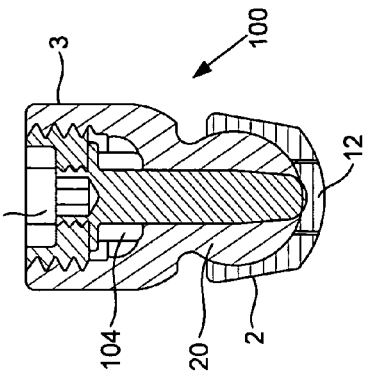
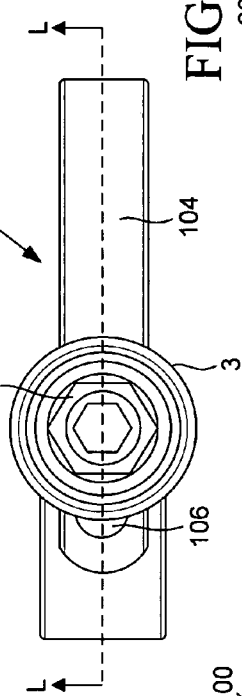
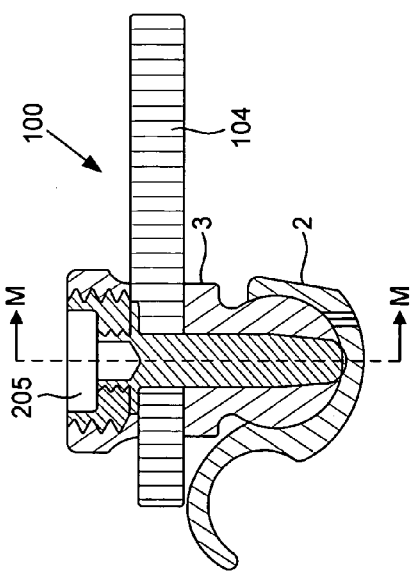

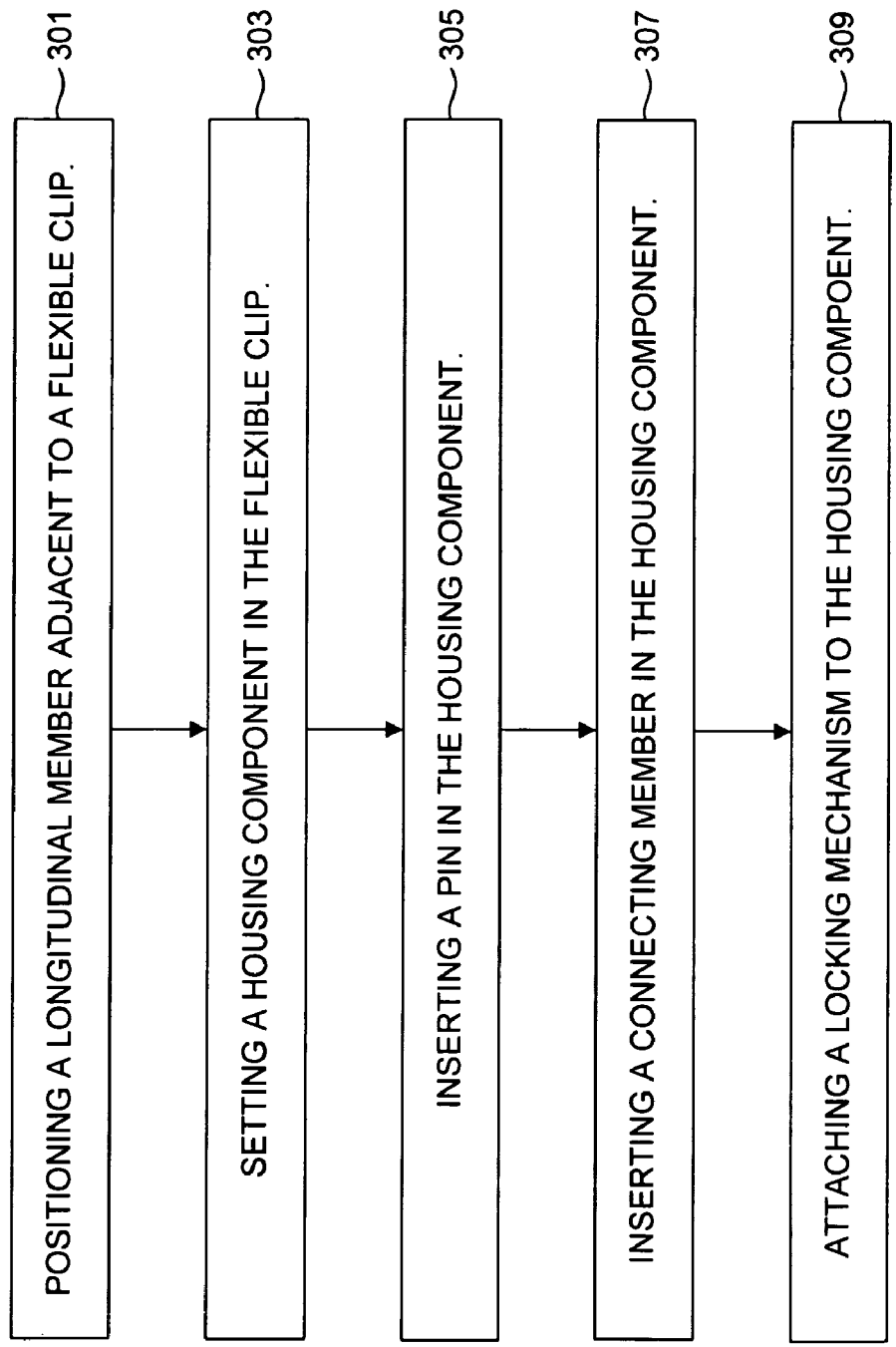

SPINAL CROSS-CONNECTOR

BACKGROUND

1. Technical Field

The embodiments herein generally relate to medical devices, and, more particularly, to implantable spinal fixation systems used for connecting cylindrical rods to each other in spinal columns.

2. Description of the Related Art

The spinal column is a highly flexible structure comprising bones and connective tissue. While, the spine is capable of multiple degrees of motion, spinal injuries or anatomical irregularities may result in spinal pathologies which limit this range of motion. Orthopedic surgeons often aim to correct spinal irregularities and restore stability to injured portions of the spine through immobilization of spinal components. Several conventional spinal implant stabilization systems such as spinal cross-connectors exist to assist doctors in immobilizing the spine. These conventional systems often include components having connective structures such as elongated rods which are positioned on opposite sides of the portion of the spinal column intended to be immobilized and are usually implemented with screws and hooks to facilitate segmental attachment of these connective structures to the posterior surfaces of the spinal laminae, through the pedicles, and into the spinal vertebral bodies. Ideally, these connective components provide the necessary mechanical stability to achieve spinal immobilization.

Most existing spinal cross-connectors consist of rods, plates, and bars linked to the longitudinal rods by coupling mechanisms with set screws, nuts, or a combination of each. Generally, these spinal cross-connectors require several subcomponents and fixation instruments to build the structures. Each additional required component or instrument necessary to assemble the connectors typically adds to the complexity and time of the surgical procedure and may effect the successful outcome of the procedure. Examples of spinal cross-connectors are described in U.S. Pat. Nos. 5,312,405; 5,334,203; and 5,498,263, the complete disclosures of which, in their entireties, are herein incorporated by reference.

However, most conventional spinal cross-connectors generally have a limited range of motion constrained by planes or axis. This tends to make them difficult to connect to the longitudinal member (i.e., transverse rod or bar) or appropriately place them around the spinal anatomy. Spinal cross-connectors usually have 3-6 degrees of freedom of movement. Accordingly, there remains a need for a new spinal cross-connector capable of having an increased number of degrees of freedom of motion and which can be easily constructed and used by a surgeon during a spinal surgical procedure.

SUMMARY

In view of the foregoing, an embodiment provides an assembly comprising a longitudinal member; a flexible clip contacting the longitudinal member; a housing component contacting the flexible clip; a locking mechanism contacting the housing component; and a connecting member contacting the housing component. Preferably, the flexible clip comprises a flexible bias member adapted to retain the longitudinal member. The flexible clip may comprise a socket portion; and a clip portion attached to the socket portion, the clip portion being adapted to retain the longitudinal member, wherein the flexible bias member extends from the clip portion to a bottom region of the socket portion.

Preferably, the locking mechanism comprises a pin portion operatively connected to the flexible clip and the housing component; and a blocker mechanism attached to the pin portion, wherein the blocker mechanism is operatively connected to the housing component, wherein the pin portion is adapted to engage the flexible bias member causing the longitudinal member to become affixed to the flexible clip. Additionally, the housing component may comprise an upper portion comprising a first hole adapted to engage the locking mechanism; and a second hole adapted to accommodate the connecting member, wherein the first hole and the second hole are transversely positioned with respect to one another, and wherein the housing component preferably comprises a bulbous end connected to the upper portion, whereby the bulbous end comprises a plurality of flexible prongs separated from one another by slots; and an opening extending through the bulbous end and extending to the first hole. The locking mechanism is preferably adapted to engage the plurality of flexible prongs causing the plurality of flexible prongs to outwardly bend and lock the housing component to the flexible clip. Furthermore, the connecting member may comprise a slot adapted to receive the locking mechanism.

Another embodiment provides a spinal cross-connector assembly comprising a connector body; a connector head adapted to engage the connector body; a pin operatively connected to the connector body and the connector head; an elongated member operatively connected to the connector head and the pin; a blocker operatively connected to the connector head and the elongated member; and a longitudinal member locked to the connector body. Preferably, the connector body comprises a flexible bias member adapted to retain the longitudinal member. The connector body preferably comprises a socket portion; and a clip portion attached to the socket portion, the clip portion being adapted to retain the longitudinal member, wherein the flexible bias member extends from the clip portion to a bottom region of the socket portion. Additionally, the pin is preferably adapted to engage the flexible bias member causing the longitudinal member to become locked to the connector body. Also, the connector head preferably comprises an upper portion comprising a first opening adapted to engage the locking mechanism; and a second opening adapted to accommodate the elongated member, wherein the first opening and the second opening are transversely positioned with respect to one another.

Preferably, the connector head comprises a bulbous end comprises a plurality of flexible prongs separated from one another by slots; and a hole extending through the bulbous end and extending to the first opening, wherein the pin is adapted to engage the plurality of flexible prongs causing the plurality of flexible prongs to outwardly bend and lock the bulbous end of the connector head to the flexible clip. Moreover, the elongated member may comprise a slot adapted to receive the pin.

Another embodiment provides a method of locking a longitudinal member to a cross-connector assembly construct, wherein the method comprises positioning a longitudinal member adjacent to a flexible clip; setting a housing component in the flexible clip; inserting a pin in the housing component, wherein the pin contacts the flexible clip; inserting a connecting member in the housing component; and attaching a locking mechanism to the housing component, wherein the locking mechanism is operatively connected to the pin. Preferably, attachment of the locking mechanism to the housing component causes the pin to engage the flexible clip thereby causing the flexible clip to lock the longitudinal member into position. Moreover, the flexible clip preferably comprises a flexible bias member, and wherein the flexible bias member is adapted to lock the longitudinal member into position.

The flexible clip may comprise a socket portion; and a clip portion attached to the socket portion, wherein the flexible bias member extends from the clip portion to a bottom region of the socket portion, and wherein the clip portion retains the longitudinal member into position. Preferably, the housing component comprises an upper portion connected to a bulbous end, wherein the upper portion comprises a first hole adapted to engage the locking mechanism; and a second hole adapted to accommodate the connecting member, wherein the first hole and the second hole are transversely positioned with respect to one another, wherein the bulbous end comprises a plurality of flexible prongs separated from one another by slots; and an opening extending through the bulbous end and extending to the first hole, wherein the pin is adapted to engage the plurality of flexible prongs causing the plurality of flexible prongs to outwardly bend and lock the housing component to the flexible clip.

Also, the method may further comprise connecting a pair of cross-connector assembly constructs using the connecting member. Moreover, the connecting member may comprise a slot, and wherein the method further comprises inserting the pin through the slot of the connecting member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3(A) illustrates a top view of a spinal cross-connector assembly according to an embodiment herein;

FIG. 3(B) illustrates a bottom view of the spinal cross-connector assembly of FIG. 3(A) according to an embodiment herein;

FIG. 3(C) illustrates a cross-sectional view of the spinal cross-connector assembly of FIG. 3(B) cut along line A-A of FIG. 3(B) according to an embodiment herein;

FIG. 4(B) illustrates a cross-sectional side view of the spinal cross-connector assembly of FIG. 4(A) cut along line B-B of FIG. 4(A) according to an embodiment herein;

FIG. 4(C) illustrates a back view of the spinal cross-connector assembly of FIG. 3(A) according to an embodiment herein;

FIG. 5(A) illustrates a perspective view of the connector body of the spinal cross-connector assembly construct of FIG. 2 according to an embodiment herein;

FIG. 5(B) illustrates a top view of the connector body of FIG. 5(A) according to an embodiment herein;

FIG. 5(C) illustrates a front view of the connector body of FIG. 5(A) according to an embodiment herein;

FIG. 5(D) illustrates a cross-sectional side view of the connector body of FIG. 5(A) cut along line C-C of FIG. 5(C) according to an embodiment herein;

FIG. 5(E) illustrates a back view of the connector body of FIG. 5(A) cut along line D-D of FIG. 5(D) according to an embodiment herein;

FIG. 7(A) illustrates a perspective view of the bar of the spinal cross-connector assembly construct of FIG. 2 according to an embodiment herein;

FIG. 7(B) illustrates a top view of the bar of FIG. 7(A) according to an embodiment herein;

FIG. 7(C) illustrates a front view of the bar of FIG. 7(A) according to an embodiment herein;

FIG. 7(D) illustrates a side view of the bar of FIG. 7(A) according to an embodiment herein;

FIG. 8(A) illustrates a perspective view of the locking pin of the spinal cross-connector assembly construct of FIG. 2 according to an embodiment herein;

FIG. 8(B) illustrates a side view of the locking pin of FIG. 8(A) according to an embodiment herein;

FIG. 8(C) illustrates a top view of the locking pin of FIG. 8(A) according to an embodiment herein;

FIG. 8(D) illustrates a cross-sectional side view of the locking pin of FIG. 8(A) cut along line H-H of FIG. 8(C) according to an embodiment herein;

FIG. 10(B) illustrates a perspective view of the transverse member of the spinal cross-connector assembly construct of FIG. 10(A) according to an alternate embodiment herein;

FIG. 10(C) illustrates a perspective view of the locking pin of the spinal cross-connector assembly construct of FIG. 10(A) according to an alternate embodiment herein;

FIG. 11(A) illustrates a perspective view of a spinal cross-connector assembly according to a second alternate embodiment herein;

FIG. 11(B) illustrates an upper perspective view of the locking mechanism of the spinal cross-connector assembly of FIG. 11(A) according to a second alternate embodiment herein;

FIG. 11(C) illustrates a lower perspective view of the locking mechanism of the spinal cross-connector assembly of FIG. 11(A) according to a second alternate embodiment herein;

FIG. 11(D) illustrates a top view of the spinal cross-connector assembly construct of FIG. 11(A) according to a second alternate embodiment herein;

FIG. 11(E) illustrates a cross-sectional side view of the spinal cross-connector assembly of FIG. 11(A) cut along line L-L of FIG. 11(D) according to a second alternate embodiment herein;

FIG. 11(F) illustrates a back view of the spinal cross-connector assembly of FIG. 11(A) cut along line M-M of FIG. 11(E) according to a second alternate embodiment herein; and FIG. 12 is a flow diagram illustrating a preferred method according to an embodiment herein.

DETAILED DESCRIPTION OF PREFERRED EMBODIMENTS

Figure 1:
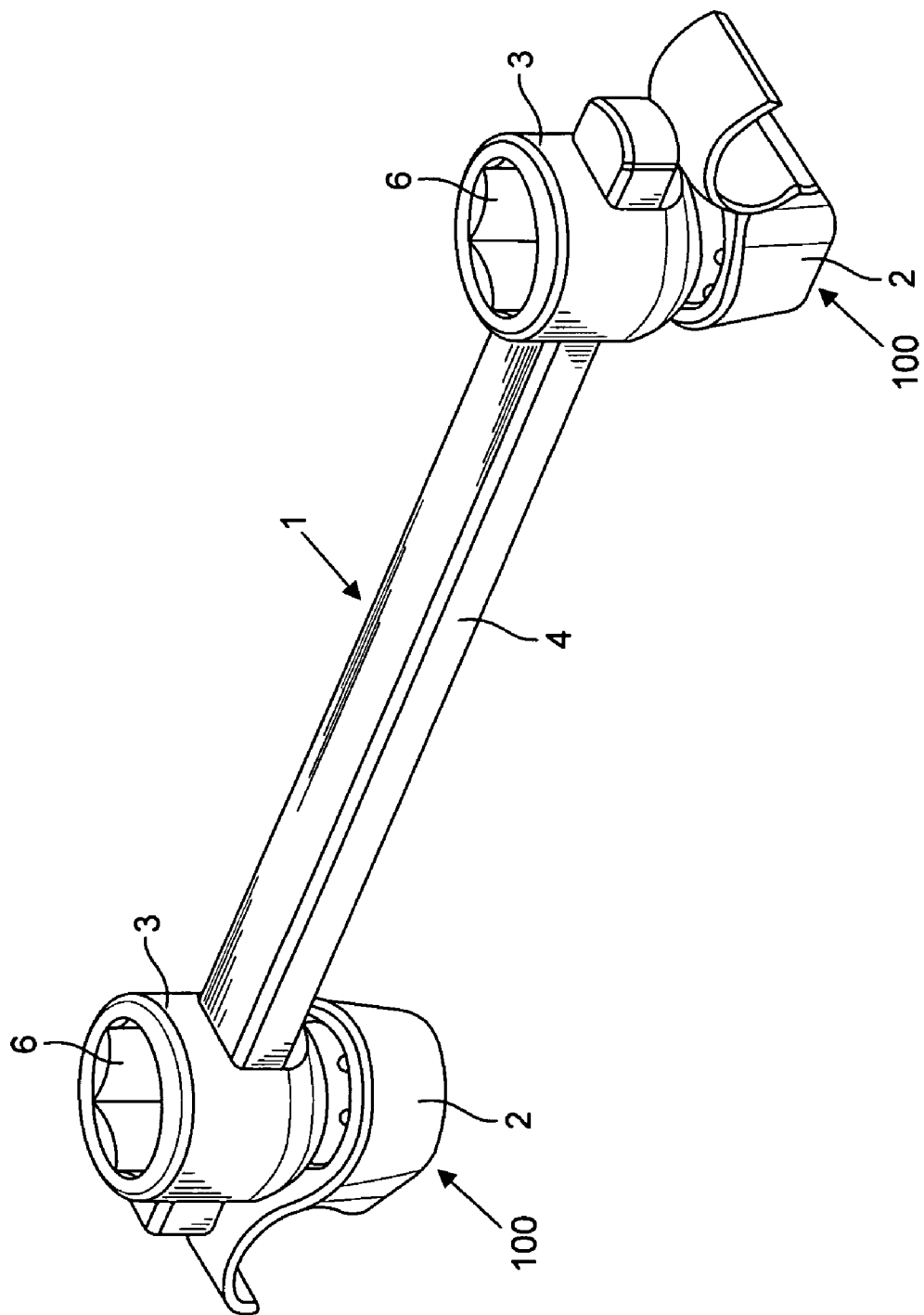
FIG. 1 illustrates a schematic diagram of a spinal cross-connector assembly according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new spinal cross-connector capable of having an increased number of degrees of freedom of motion and which can be easily constructed and used by a surgeon during a spinal surgical procedure. The embodiments herein achieve this by providing a top loading spinal cross-connector having a one-step locking mechanism and providing six degrees of freedom for easier placement over varied anatomy. Referring now to the drawings, and more particularly to FIGS. 1 through 12, where similar reference characters denote corresponding features consistently throughout the figures, there are shown preferred embodiments.

Figure 2:
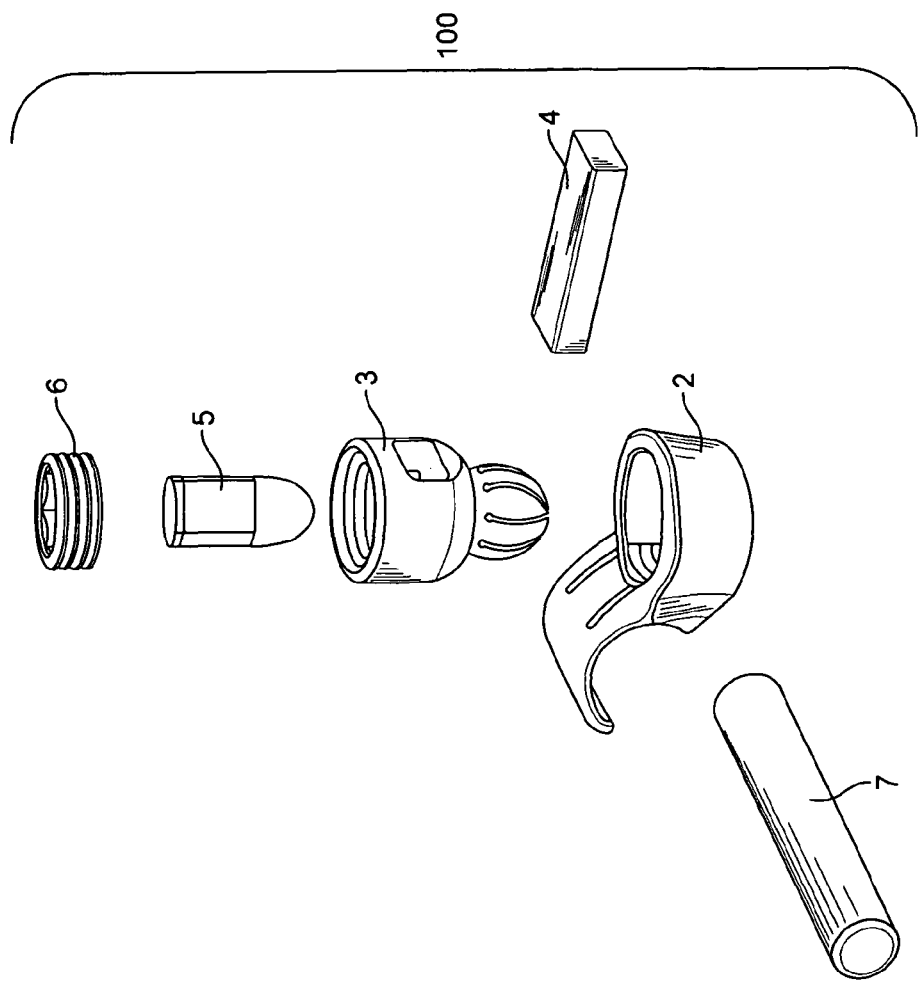
FIG. 2 illustrates an exploded view of the spinal cross-connector assembly construct of FIG. 1 according to an embodiment herein.

FIG. 1 illustrates a spinal cross-connector assembly 1 according to an embodiment herein. When used in a surgical procedure, the assembly 1 generally comprises two separate constructs 100 connected by a transverse member 4 (for example, a bar, rod, or other connecting member geometry). As further illustrated in FIG. 2, each of the constructs 100 comprises a connector body 2 operatively connected to a connector head 3, which is dimensioned and configured to receive a locking pin 5, a set screw 6, and the transverse member 4. The connector body 2 is dimensioned and configured to engage a longitudinal member 7 (for example, a rod, bar, or other geometries). With reference to FIGS. 1 and 2, both constructs 100 of the spinal cross-connector assembly 1 are placed on the opposing longitudinal members 7 of the spinal fusion construct. Preferably, each construct 100 of the spinal cross-connector assembly 1 is polyaxial with respect to its motion relative to a fixed axis and as such may be adjusted for optimum placement within the spinal cavity (not shown).

FIGS. 3(A) through 4(C) illustrate several views of one of the constructs 100 of the spinal cross-connector assembly 1 of FIG. 1. In FIGS. 3(A), 4(A), and 4(B) the dotted arrows refer to the respective directions of the range of motion of the connector head 3 and transverse member 4. The heavy arrows at the bottom of FIG. 4(B) refer to the forces (i.e., compression) caused by the construct 100 when it engages the longitudinal member 7. The horizontal heavy arrows in FIG. 4(B) refer to the expanding forces, $F_e$, of the connector head 3 while the heavy arrow that points down refers to the pushing force, $F_p$, of the locking pin 5. These forces also aid in keeping the construct 100 in a locked position (i.e., retaining the transverse member 4 and longitudinal member 7 intact once they are set into place). All of the components of the construct 100 can be seen in the cross-sectional view of FIG. 3(C) taken along line A-A of FIG. 3(B). In this view, the set screw 6 is set into place, which creates a downward force on the transverse member 4 and locking pin 5 to retain them into a proper set position in the connector head 3 (with the ends of the transverse member 4 extending out of the connector head 3). This view also illustrates the connector head 3 set into place within the connector body 2, which then holds the longitudinal member 7 in place.

Figure 4A:
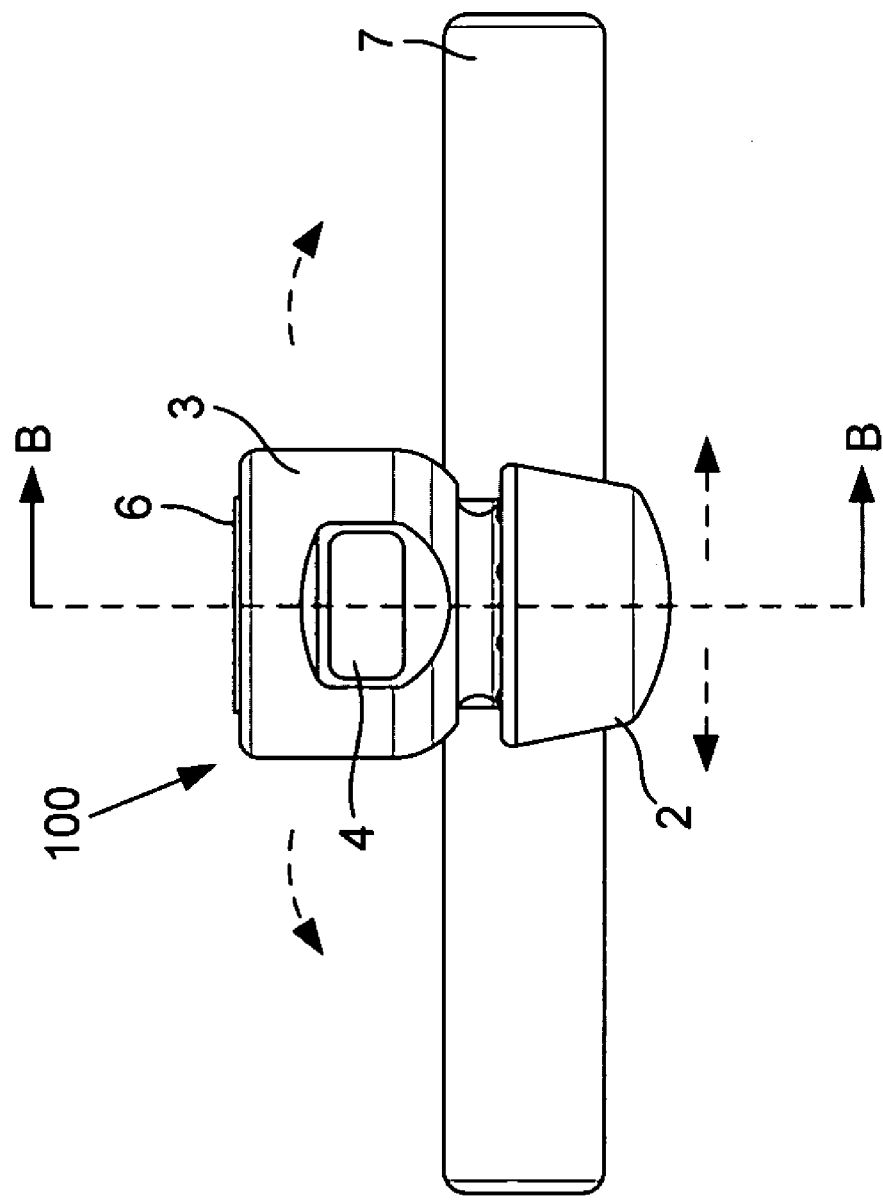
FIG. 4(A) illustrates a back view of the spinal cross-connector assembly of FIG. 3(A) according to an embodiment herein.

All of the components set into place in the construct 100 can be seen in the cross-sectional view of FIG. 4(B) taken along line B-B of FIG. 4(A). FIG. 4(C) best illustrates the engagement of the longitudinal member 7 with the connector body 2.

The several individual sub-components of the construct 100 of the spinal cross-connector assembly 1 of FIGS. 1 through 4(C) are described below. FIGS. 5(A) through 5(E) illustrate several views of the connector body 2 according to an embodiment herein. The connector body 2 is generally embodied as a one-piece construct (although multiple pieces fixed to one another are possible) and comprises a socket portion 8 attached to a longitudinal member receiving clip 9. The socket portion 8 comprises a generally hollowed inner socket 10 defined by an inner socket wall 15, an inner socket base 16, and an upper lip 13. An outer socket wall 14 provides the outer definition of the socket portion 8 of the connector body 2. The receiving clip 9 comprises a curved upper surface 11 having a concave portion 18 positioned on the underside of the curved upper surface 11. The concave portion 18 is dimensioned and configured to receive the longitudinal member 7 (of FIGS. 2 through 4(C)).

With reference to FIG. 5(B), which illustrates a top view of the connector body 2, the inner socket base 16 of the socket portion 8 is generally circular in shape and it is on this base 16 where the connector head 3 and locking pin 5 (of FIGS. 1 through 4(C)) rest. The inner socket base 16 further includes a gap 17, which creates a separation between the inner socket base 16 and a bias member 12 of the connector body 2. The bias member 12 may be configured as a spring, flange, or flexible structure. The gap 17 extends up to and in the receiving clip 9, and when viewed from the top (as in FIG. 5(B)) the gap 17 may appear to be V-shaped although other shapes are possible, and the embodiments herein are not limited to any particular shape or geometry. Generally, the bias member 12 is an extension of the receiving clip 9 as it is retained in a cantilever manner to the connector body 2 only by the receiving clip 9 and does not contact the socket portion 8 due to the gap 17. Preferably, the thickness of the gap 17 is uniform, but may include a slightly larger gap area towards the bottom of the gap 17 (i.e., bottom of the V-shape).

FIG. 5(D) illustrates a cross-sectional side view of the connector body 2 of FIG. 5(A) taken along line C-C of FIG. 5(C). In this view, the relative thicknesses of the socket portion 8 and receiving clip 9 can be seen as well as the relative depth of the gap 17. Additionally, the configuration of the concave portion 18 of the receiving clip 9 can be seen as generally matching the cylindrical configuration of the longitudinal member 7 (of FIGS. 2 through 4(C)). FIG. 5(E) illustrates a back view of the connector body 2 of FIG. 5(A) taken along line D-D of FIG. 5(D), and further illustrates the general configuration of the gap 17.

FIGS. 6(A) through 6(E) illustrate several views of the connector head 3 of the spinal cross-connector assembly construct 100 of FIG. 2 according to an embodiment herein. Preferably, the connector head 3 is a one-piece construct (although multiple pieces fixed to one another are possible) and comprises an upper portion 19 connected to a lower bulbous end 20. The upper portion 19 is defined by a generally curved outer wall 21 having an upper cavity hole 22 and a bar receiving hole 23 configured therein. Preferably, the upper cavity hole 22 is positioned along a longitudinal axis of the connector head 3 and the bar receiving hole 23 is positioned along an axis transverse to the longitudinal axis of the connector head 3, and thus the upper cavity hole 22 is preferably transverse to the bar receiving hole 23. The bar receiving hole 23 extends through the outer wall 21 of the connector head 3 and the upper cavity hole 22 extends longitudinally through the connector head 3 and terminates with an opening 26 at the bottom of the bulbous end 20 of the connector head 3. Threads 28 are configured in the upper portion 19 of the connector head 3 and are dimensioned and configured to receive the set screw 6 (of FIGS. 1 through 4(C)).

An inner connector base 27 generally separates the upper portion 19 of the connector head 3 from the bulbous end 20 of the connector head 3, wherein the inner connector base 27 is preferably flat to facilitate an even positioning of the transverse member 4 (of FIGS. 1 through 4(C)). Moreover, the bulbous end 20 preferably comprises a generally spherical configuration having a plurality of downward-turned prongs 24 spaced apart from one another by slots 25. The prongs 24 are flexible to allow expansion of the bulbous end 20 of the connector head 3 into the inner socket 10 of the connector body 2. Additionally, a pin cavity 29 is configured in the bulbous end 20 of the connector head 3 to accommodate the locking pin 5 (of FIGS. 2 through 4(C)), wherein the upper part of the pin cavity 29 begins at the position of the inner connector base 27, and the lower part of the pin cavity 29 terminates at the opening 26 in the bulbous end 20 of the connector head 3.

Figure 6B:
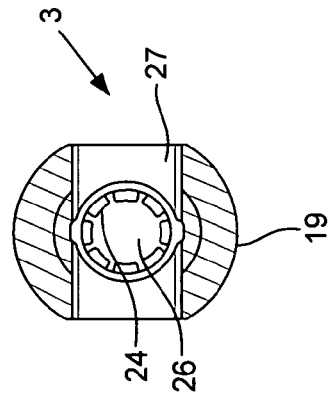
FIG. 6(B) illustrates a side view of the connector head of FIG. 6(A) according to an embodiment herein.
Figure 6A:
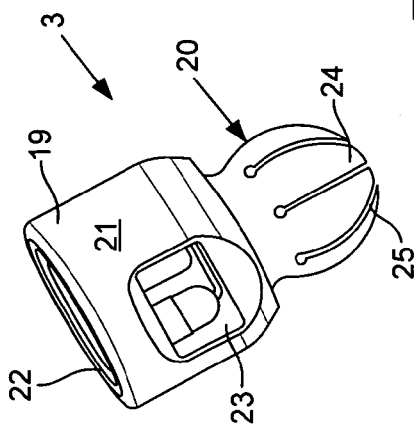
FIG. 6(A) illustrates a perspective view of the connector head of the spinal cross-connector assembly construct of FIG. 2 according to an embodiment herein.
Figure 6E:
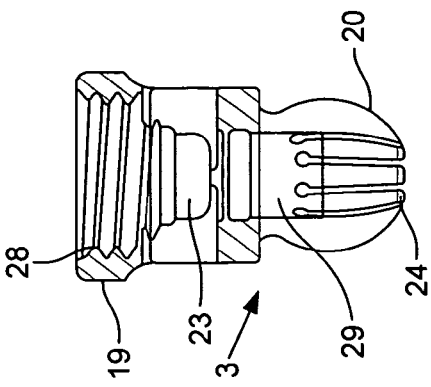
FIG. 6(E) illustrates a cross-sectional side view of the connector head of FIG. 6(A) cut along line G-G of FIG. 6(D) according to an embodiment herein.
Figure 6D:
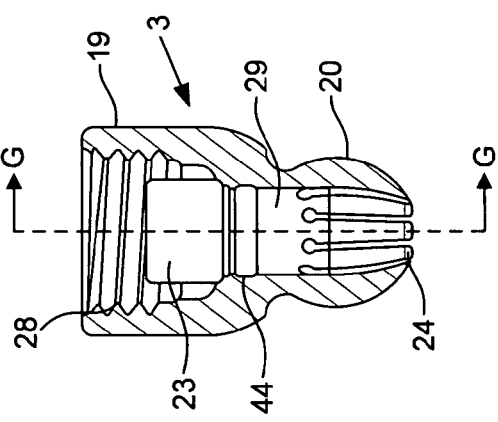
FIG. 6(D) illustrates a cross-sectional front view of the connector head of FIG. 6(A) cut along line F-F of FIG. 6(B) according to an embodiment herein.
Figure 6C:
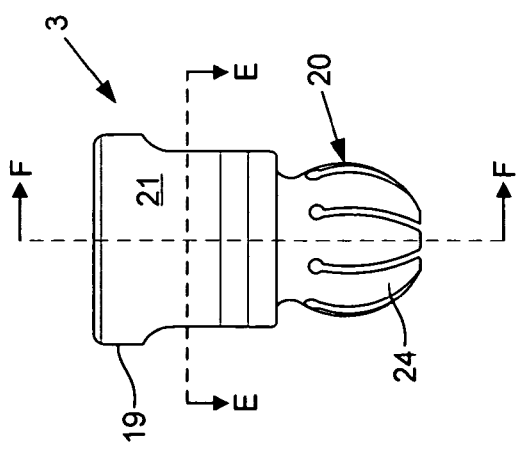
FIG. 6(C) illustrates a cross-sectional top view of the connector head of FIG. 6(A) cut along line E-E of FIG. 6(B) according to an embodiment herein.

FIG. 6(C) illustrates a cross-sectional top view of the connector head 3 of FIG. 6(A) taken along line E-E of FIG. 6(B). In this view, the relative thickness of the upper portion 19 of the connector head 3 is illustrated. FIG. 6(D) illustrates a cross-sectional front view of the connector head 3 of FIG. 6(A) taken along line F-F of FIG. 6(B), and FIG. 6(E) illustrates a cross-sectional side view of the connector head 3 of FIG. 6(A) cut along line G-G of FIG. 6(D). In these views, the threads 28 and pin cavity 29 can best be seen.

FIGS. 7(A) through 7(D) illustrate several views of the transverse member 4 (of FIGS. 1 through 4(C)) according to an embodiment herein. The transverse member 4 generally comprises a generally uniform elongated one-piece body 30 (although multiple pieces fixed to one another are possible) with a pair of distal ends 31, 32 comprising a first end 31 distally located to a second end 32. The transverse member 4 is dimensioned and configured to fit through the bar receiving hole 23 of the connector head 3 and rest on the inner socket base 16 of the connector head 3 (of FIGS. 6(A) through 6(E)). The bar receiving hole 23 may be configured to snugly fit the transverse member 4, or alternatively, the bar receiving hole 23 may be configured wider than the width of the transverse member 4 to allow for some "slop" for additional range of motion of the transverse member 4.

FIGS. 8(A) through 8(D) illustrate several views of the locking pin 5 of the spinal cross-connector assembly construct 100 of FIG. 2 according to an embodiment herein. The locking pin 5 is preferably embodied as a one-piece construct (although multiple pieces fixed to one another are possible). The locking pin 5 comprises a lower end 33 terminating with a tip 39. Extending from the lower end 33 and distally away from the tip 39 is a plurality of upper members 34 separated from one another by slots 36. Preferably, the shape of the upper members 34 follows the contour of the shape of the lower end 33 of the locking pin 5, wherein the overall contour of the locking pin 5 is dimensioned and configured to fit into the pin cavity 29 of the connector head 3 (of FIGS. 6(D) and 6(E)). A central hole 35 is configured in the locking pin 5 and in between the plurality of upper members 34 such that the combination of the central hole 35 and slots 36 create prong-like upper members 34. The central hole 35 terminates with a central hole base 38, which acts as a positional separation between the lower end 33 of the locking pin 5 and the upper members 34 of the locking pin 5. Additionally a lip 37 is configured on each of the upper members 34, wherein the lips 37 of all of the upper members 34 are aligned to one another to form a substantially circular shape when viewed from the top as illustrated in FIG. 8(C). The lips 37 of the upper members 34 are adapted to lock the locking pin 5 into connector head 3 (of FIGS. 6(A) through 6(E)) to prevent back-out of the connector head 3 from the connector body 2 (of FIGS. 5(A) through 5(E)). Lips 37 fit into the undercut diameter slot 44 of the connector head shown 3 in FIG. 6(D). FIG. 8(D) illustrates a cross-sectional side view of the locking pin 5 of FIG. 8(A) taken along line H-H of FIG. 8(C). In this view, the edges 42 of the upper members 34 can be seen as well as the preferred conical shape (although other shapes are possible) of the central hole base 38.

Figure 9B:
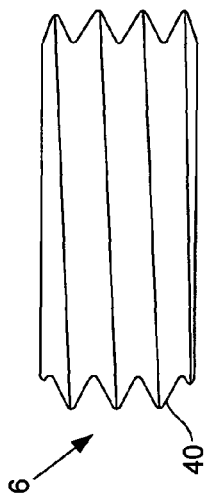
FIG. 9(B) illustrates a side view of the set screw of FIG. 9(A) according to an embodiment herein.
Figure 9D:
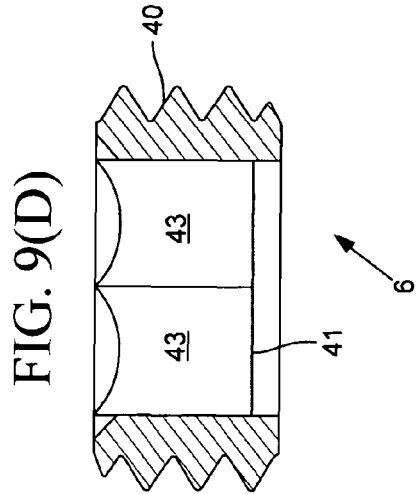
FIG. 9(D) illustrates a cross-sectional side view of the set screw of FIG. 9(A) cut along line I-I of FIG. 9(C) according to an embodiment herein.
Figure 9A:
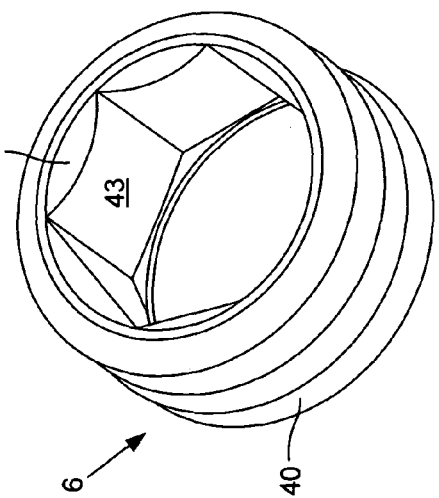
FIG. 9(A) illustrates a perspective view of the set screw of the spinal cross-connector assembly construct of FIG. 2 according to an embodiment herein.
Figure 9C:
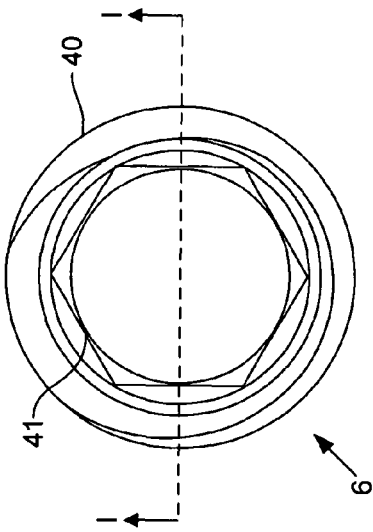
FIG. 9(C) illustrates a top view of the set screw of FIG. 9(A) according to an embodiment herein.

FIGS. 9(A) through 9(D) illustrate several views of the set screw 6 of the spinal cross-connector assembly 1 of FIG. 1 according to an embodiment herein. Generally, the set screw 6 may be any type of blocker used to retain the transverse member 4 and locking pin 5 in place in the connector head 3 (of FIGS. 2 through 4(C)). In one embodiment, the set screw 6 comprises threads 40 positioned around an outer periphery of the set screw 6 and dimensioned and configured to engage the threads 28 of the connector head 3 (of FIGS. 6(D) and 6(E)). Moreover, the set screw 6 comprises a fastening feature 41, which may be configured to accommodate a screwdriver (hex, torx, flat-head, Phillips, etc.) or similar mechanism. Alternatively, if the threads 28 of the connector head 3 (of FIGS. 6(D) and 6(E)) are configured along the outer wall 21 of the connector head 3, then the corresponding threads 40 of the set screw 6 are configured along the inner wall 43 of the set screw 6 of FIG. 9(A). FIG. 9(D) illustrates a cross-sectional side view of the set screw 6 of FIG. 9(A) cut along line I-I of FIG. 9(C), which further shows the inner wall 43 of the set screw 6.

With respect to FIGS. 1 through 9(C), in a preferred embodiment, the transverse member 4 is bendable and may be bent if desired to avoid interference with the spinal anatomy (not shown). Moreover, the bendable transverse member 4 may be cut to length if desired to avoid protrusion into soft tissue or can be pre-cut and pre-assembled to various sizes. Furthermore, each polyaxial connector head 3 is locked into place by its internal preloaded set screw 6.

Accordingly, the set screw 6 locks the polyaxial connector head 3 into position as well as the connector body 2 to the longitudinal member 7 all in one locking step. This occurs by placing the bulbous end 20 of the connector head 3 into the inner socket 10 of the socket portion 8 of the connector body 2. Next, the locking pin 5 is placed into the pin cavity 29 (lower end 33 of the locking pin 5 is placed first) of the connector head 3. Then, the transverse member 4 is placed in the bar receiving hole 23 of the connector head 3. Thereafter, the longitudinal member 7 is placed into position in the concave portion 18 of the receiving clip 9 of the connector body 2.

After this, in a one-step locking procedure, the set screw 6 is fastened into place in the connector head 3 with the threads 40 of the set screw 6 engaging the threads 28 of the connector head 3. The tightening of the set screw 6 causes the body 30 of the transverse bar 4 to exert a force on upper members 34 of the locking pin 5, which causes the tip 39 of the lower end 33 of the locking pin 5 to exert a force on the prongs 24 of the bulbous end 20 of the connector head 3, which causes the bulbous end 20 of the connector head 3 to expand in the inner socket 10 of the socket portion 8 of the connector body 2. This also causes the tip 39 to protrude through the opening 26 of the bulbous end 20 of the connector head 3. This, in turn, causes the bias member 12 of the connector body 2 to bend away from the connector head 3 and against the longitudinal member 7, which is positioned in the concave portion 18 of the receiving clip 9 of the connector body 2 thereby securing the longitudinal member 7 into a set position in the concave portion 18 of the receiving clip 9. As such, this locking procedure locks the connector head 3 and longitudinal member 7 to the connector body 2 as well as the transverse member 4 and locking pin 5 to the connector head 3.

Figure 10A:
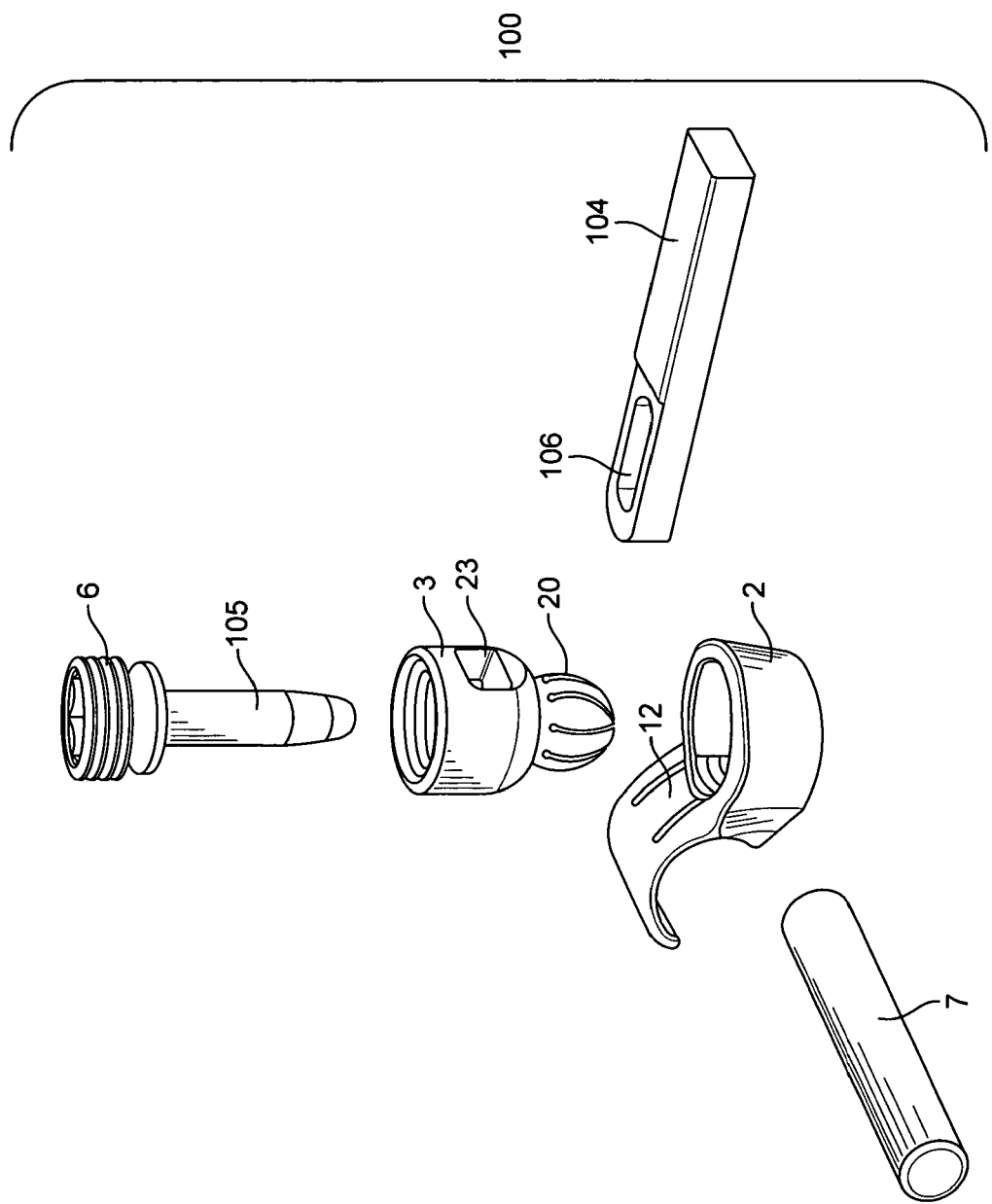
FIG. 10(A) illustrates an exploded view of a spinal cross-connector assembly construct according to an alternate embodiment herein.

In another embodiment, the construct 100 may include a slightly altered transverse member 104 and locking pin 105 as shown in FIG. 10(A). Here, the connector head 3 fits into the connector body 2 as with the previous embodiment. However, as illustrated in FIG. 10(B), the transverse member 104 includes a slot 106 configured in each distal end 31, 32 of the transverse member 104. FIG. 10(C) illustrates a perspective view of the alternate locking pin 105, which comprises a generally planar upper portion 107 and a stem portion 108 extending from the upper portion 107. The stem portion 108 ends with a generally tapered section 109. The locking pin 105 is configured to fit into the pin cavity 29, which is configured in the bulbous end 20 of the connector head 3 (of FIGS. 6(D) and 6(E)).

Figure 10F:
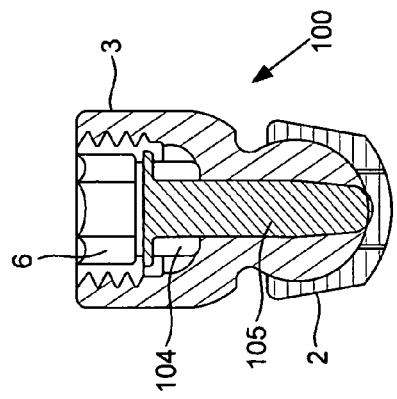
FIG. 10(F) illustrates a back view of the spinal cross-connector assembly of FIG. 10(E) cut along line K-K of FIG. 10(E) according to an alternate embodiment herein.
Figure 10D:
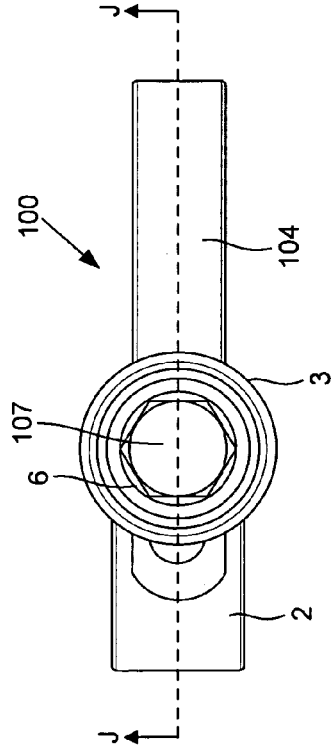
FIG. 10(D) illustrates a top view of the assembled spinal cross-connector assembly construct of FIG. 10(A) according to an alternate embodiment herein.
Figure 10E:
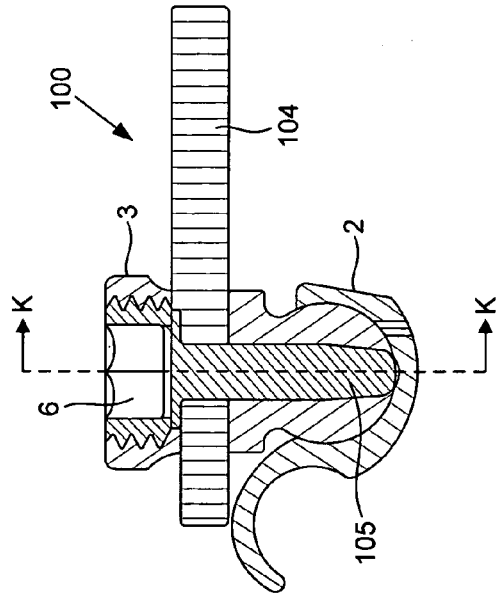
FIG. 10(E) illustrates a cross-sectional side view of the spinal cross-connector assembly of FIG. 10(D) cut along line J-J of FIG. 10(D) according to an alternate embodiment herein.

Then, with respect to FIGS. 10(D) through 10(F), the transverse member 104 is inserted into the bar receiving hole 23 of the connector head 3 and the locking pin 105 is inserted in the connector head 3 and through the slot 106 of the transverse member 104. The set screw 6 is then connected to the connector head 3. This embodiment allows for a more secured locking of the transverse member 104 into place in the connector head 3. However, the width and length of the slot 106 is preferably configured larger than the diameter of the locking pin 105 so as to allow for an adjustable positioning of the transverse member 104 in the connector head 3. The positioning of the locking pin 105 with respect to the transverse member 104 is best shown in FIGS. 10(E) and 10(F) where the side view of FIG. 10(E) is taken along line J-J of FIG. 10(D) and the back view of FIG. 10(F) is taken along line K-K of FIG. 10(E). The manner of the bulbous end 20 of the connector head 3 expanding in the connector body 2 due to the insertion of the locking pin 105 and clamping force of the set screw 6 thereby causing actuation of the bias member 12 is similar in the alternate embodiment as it was for the preferred embodiment.

Still another alternate embodiment is illustrated in FIGS. 11(A) through 11(F). Here, a combined locking mechanism 205 is provided to fit through the slot 106 of the transverse member 104 and fit into the connector head 3 and engage the connector body 2. The locking mechanism 205 is preferably configured as a one-piece structure (either threaded together or molded together) comprising an upper blocker portion 206 and a stem portion 208 extending from the blocker portion 206. The stem portion 208 terminates with a generally tapered end 209. The manner of the bulbous end 20 of the connector head 3 expanding in the connector body 2 due to the insertion and clamping force of the locking mechanism 105 thereby causing actuation of the bias member 12 is similar in the second alternate embodiment as it was for the preferred embodiment and the first alternate embodiment. The second alternate embodiment allows for fewer component parts and an easier assembly process. The positioning of the locking pin 205 with respect to the transverse member 104 is best shown in FIGS. 11(E) and 11(F) where the side view of FIG. 11(E) is taken along line L-L of FIG. 11(D) and the back view of FIG. 11(F) is taken along line M-M of FIG. 11(E).

In other alternative embodiments, the geometry of the connector body 2 may be modified for customized angle placement of the longitudinal member 7 on the connector body 2. Additionally, the inner socket 10 of the connector body 2 may be positioned at various locations in the connector body 2 to provide varied offsets or heights of initial position for the assembly 1. Also, the elongated connecting transverse member 4 may be dimensioned and configured to fit over the connector head 3 and be locked by the set screw 6. Furthermore, the materials for all components in the assembly 1 may comprise any suitable grades of metal, polymers, or shape-memory materials.

FIG. 12, with reference to FIGS. 1 through 11(F), illustrates a flow diagram of a method of locking a longitudinal member 7 to a cross-connector assembly construct 100, wherein the method comprises positioning (301) a longitudinal member 7 adjacent to a flexible clip 2; setting (303) a housing component 3 in the flexible clip 2; inserting (305) a pin 5 in the housing component 3, wherein the pin 5 contacts the flexible clip 2; inserting (307) a connecting member 4 in the housing component 3; and attaching (309) a locking mechanism 6 to the housing component 3, wherein the locking mechanism 6 is operatively connected to the pin 5.

Preferably, attachment of the locking mechanism 6 to the housing component 3 causes the pin 5 to engage the flexible clip 2 thereby causing the flexible clip 2 to lock the longitudinal member 7 into position. Moreover, the flexible clip 2 preferably comprises a flexible bias member 12, and wherein the flexible bias member 12 is adapted to lock the longitudinal member 7 into position.

Preferably, the flexible clip 2 comprises a socket portion 8 and a clip portion 9 attached to the socket portion 8, wherein the flexible bias member 12 extends from the clip portion 9 to a bottom region 16 of the socket portion 8, and wherein the clip portion 9 retains the longitudinal member 7 into position. Preferably, the housing component 3 comprises an upper portion 19 connected to a bulbous end 20, wherein the upper portion 19 comprises a first hole 22 adapted to engage the locking mechanism 6; and a second hole 23 adapted to accommodate the connecting member 4, wherein the first hole 22 and the second hole 23 are transversely positioned with respect to one another, wherein the bulbous end 20 comprises a plurality of flexible prongs 24 separated from one another by slots 25; and an opening 26 extending through the bulbous end 20 and extending to the first hole 22, wherein the pin 5 is adapted to engage the plurality of flexible prongs 24 causing the plurality of flexible prongs 24 to outwardly bend and lock the housing component 3 to the flexible clip 2.

Also, the method may further comprise connecting a pair of cross-connector assembly constructs 100 using the connecting member 4. Moreover, the connecting member 4 may comprise a slot 106, and wherein the method further comprises inserting the pin 5 through the slot 106 of the connecting member 4.

Generally, the embodiments herein provide a polyaxial cross-connector (transverse connector/rod crosslink) assembly 1 adapted to connect the longitudinal members 7 of a spinal fusion construct 100 in an easy an efficient manner. The embodiments herein augment the conventional assemblies by providing an assembly that is stiffer and stronger under torsional loads than conventional designs. The assembly 1 generally comprises a flexible clip 9 with a socket 10 adapted to receive the polyaxial connector head 2 which houses the bendable transverse member 4. Moreover, the embodiments herein have a minimum of two to a maximum of nine degrees (and preferably six degrees) of freedom depending on whether the bendable transverse member 4 is embodied as a rod or bar. Furthermore, the assembly 1 may be packaged pre-assembled prior to use during surgery.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An assembly comprising:
    a longitudinal member;
    a flexible clip contacting said longitudinal member, wherein said flexible clip comprises:
        a socket portion comprising a concave inner socket portion and a substantially closed bottom;
        a first flexible member adjacent to a side of said socket portion; and
        a second flexible member that flexes with respect to said first flexible member and extends from said first flexible member to the bottom of said socket portion such that said second flexible member is structurally separated from said bottom of said socket portion by a gap;
    a housing component contacting said flexible clip, wherein said housing component comprises:
        an upper portion comprising a first opening and a second opening, wherein said first opening and said second opening are transversely positioned with respect to one another;
        a lower portion; and
        an outwardly protruding and expandable spherical bulbous end extending from said lower portion, wherein said bulbous end fits into said socket portion of said flexible clip, wherein said socket portion substantially cups said bulbous end with said concave inner socket portion, and wherein said bulbous end comprises:
            a plurality of flexible prongs separated from one another by slots; and
            a hole extending through said bulbous end and extending to said first opening;
    a locking mechanism contacting said housing component, wherein said locking mechanism engages said bulbous end of said housing component causing said bulbous end to outwardly expand and lock said bulbous end of said housing component to said flexible clip; and
    a connecting member contacting said housing component.

2. The assembly of claim 1, wherein said second flexible member retains said longitudinal member to said first flexible member.

3. The assembly of claim 1,
    wherein said first flexible member retains said longitudinal member to said second flexible member.

4. The assembly of claim 1, wherein said locking mechanism comprises:
    a pin portion operatively connected to said flexible clip and said housing component; and
    a blocker mechanism attached to said pin portion, wherein said blocker mechanism is operatively connected to said upper portion of said housing component,
    wherein said pin portion engages said second flexible member causing said longitudinal member to become affixed to said flexible clip.

5. The assembly of claim 1,
    wherein said second flexible member extends from said first flexible member to a bottom region of said socket portion.

6. The assembly of claim 4,
    wherein said pin engages said second flexible member causing said second flexible member to extend away from said socket portion and causing said longitudinal member to become locked to said flexible clip.

7. The assembly of claim 1, wherein said second flexible member is dimensioned and configured to contour to a shape of said socket portion.

8. The assembly of claim 1, wherein said connecting member comprises a slot that receives said locking mechanism.

9. A spinal cross-connector assembly comprising:
    a connector body comprising:
        a socket portion comprising an open top, a concave inner socket portion, and a substantially closed bottom;
        a flexible clip portion adjacent to a side of said socket portion; and
        a flexible bias member that flexes with respect to said flexible clip portion and extends from said flexible clip portion to the bottom of said socket portion such that said flexible bias member is structurally separated from said bottom of said socket portion by a gap;
    a connector head that engages said connector body, wherein said connector head comprises:
        an upper portion comprising:
            a first opening that engages a blocker; and
            a second opening that accommodates an elongated member, wherein said first opening and said second opening are transversely positioned with respect to one another,
        a lower portion; and
        an outwardly protruding and expandable spherical bulbous end extending from said lower portion, wherein said bulbous end fits into said socket portion of said flexible clip portion, wherein said socket portion substantially cups said bulbous end with said concave inner socket portion, and wherein said bulbous end comprises:
- a plurality of flexible prongs separated from one another by slots; and
- a hole extending through said bulbous end and extending to said first opening;

a pin operatively connected to said connector body and said connector head;

wherein said elongated member is operatively connected to said connector head and said pin, wherein said blocker is operatively connected to said connector head and said elongated member.

10. The spinal cross-connector assembly of claim 9, further comprising a longitudinal member locked to said connector body, wherein said flexible bias member retains said longitudinal member to said flexible clip portion.

11. The spinal cross-connector assembly of claim 10, wherein said flexible clip portion retains said longitudinal member, and wherein said flexible bias member is dimensioned and configured to contour to a shape of said flexible clip portion and said socket portion.

12. The spinal cross-connector assembly of claim 10, wherein said pin engages said flexible bias member causing said flexible bias member to extend away from said connector body and causing said longitudinal member to become locked to said connector body.

13. The spinal cross-connector assembly of claim 9, wherein said pin engages said plurality of flexible prongs causing said plurality of flexible prongs to outwardly bend and lock said bulbous end of said connector head to said concave inner socket portion.

14. The spinal cross-connector assembly of claim 9, wherein said elongated member comprises a slot that receives said pin.

15. A method of locking a longitudinal member to a spinal cross-connector assembly, said method comprising:
- positioning a longitudinal member adjacent to a connector body, wherein said connector body comprises:
  - a socket portion comprising a concave inner socket portion and a substantially closed bottom base;
  - a first flexible member adjacent to a side of said socket portion; and
  - a second flexible member that flexes with respect to said first flexible member and extends from said first flexible member to the bottom base of said socket portion such that said second flexible member is structurally separated from said bottom base of said socket portion by a gap;
- setting a connector head in said connector body, wherein said connector head comprises:
  - an upper portion comprising a first opening and a second opening, wherein said first opening and said second opening are transversely positioned with respect to one another; and
  - a lower portion comprising an outwardly protruding and expandable spherical bulbous end that fits into said socket portion of said connector body, and wherein said socket portion cups said bulbous end with said concave inner socket portion, wherein said bulbous end comprises a plurality of flexible prongs separated from one another by slots; and a third opening extending through said bulbous end and extending to said first opening;
- inserting a locking mechanism in said connector head and through said bulbous end, wherein said locking mechanism engages said bulbous end causing said bulbous end to outwardly expand and lock said bulbous end in said concave inner socket portion; and
- inserting an elongated transverse member in said connector head.

16. The method of claim 15, further comprising using said second flexible member to retain said longitudinal member to said first flexible member.

17. The method of claim 15, further comprising using said first flexible member to retain said longitudinal member to said second flexible member.

18. The method of claim 15, wherein in the inserting process, said locking mechanism comprises:
- a stem portion operatively connected to said connector body and said connector head; and
- a blocker mechanism attached to said stem portion, wherein said blocker mechanism is operatively connected to said upper portion of said connector head,
- wherein said stem portion engages said second flexible member causing said longitudinal member to become affixed to said connector body.

19. The method of claim 15, wherein said second flexible member extends from said first flexible member to said bottom base of said socket portion.

20. The method of claim 18, wherein said stem portion engages said second flexible member causing said second flexible member to extend away from said socket portion and causing said longitudinal member to become locked to said first flexible member.

21. The method of claim 15, wherein said second flexible member is dimensioned and configured to contour to a shape of said socket portion.

* * * * *